United States Patent [19]

Fukuhara

[11] Patent Number: 5,174,967
[45] Date of Patent: Dec. 29, 1992

[54] AROMA GENERATING DEVICE USING AN AIR CONDITIONING APPARATUS

[75] Inventor: Hiroshi Fukuhara, Yokohama, Japan

[73] Assignee: Fukuhara Seisakusho Co., Ltd., Yokohama, Japan

[21] Appl. No.: 614,694

[22] Filed: Nov. 15, 1990

Related U.S. Application Data

[63] Continuation of Ser. No. 368,717, Jun. 21, 1989, abandoned.

[30] Foreign Application Priority Data

Mar. 3, 1989 [JP] Japan .................... 1-24971[U]

[51] Int. Cl.⁵ .............................................. A61L 9/14
[52] U.S. Cl. ............................................... 422/124
[58] Field of Search ................... 126/113; 422/124; 454/337

[56] References Cited

U.S. PATENT DOCUMENTS

| | | | |
|---|---|---|---|
| 2,472,011 | 5/1949 | Graham | 422/124 |
| 2,523,373 | 9/1950 | Jennings et al. | 422/124 |
| 4,780,253 | 10/1988 | Fukuhara et al. | 422/124 X |
| 5,023,020 | 6/1991 | Machida et al. | 422/124 X |

FOREIGN PATENT DOCUMENTS

| | | | |
|---|---|---|---|
| 467472 | 4/1946 | Canada | 422/124 |
| 2448930 | 10/1980 | France | 422/124 |

*Primary Examiner*—Harold Joyce
*Attorney, Agent, or Firm*—Cushman, Darby & Cushman

[57] ABSTRACT

An apparatus and method for filling a defined space with a desired aroma. The apparatus may be attached to an individual air-conditioner unit or may be used in conjunction with an air-conditioning system for an entire building. The ability to incorporate the nozzle of the air-conditioner within the system or unit allows production expenses to be reduced (the nozzle does not have to be made large). The air-conditioner moves the air with the aroma therein while the defined space is being heated or cooled. With a single unit, output from the aroma generating device is moved by the unit's fan into the defined space. In a building, the aroma generating apparatus is built into place prior to ducts provided for carrying air from a central air-conditioner to rooms wihtin the building.

8 Claims, 3 Drawing Sheets

AROMA GENERATING DEVICE USING AN AIR CONDITIONING APPARATUS

This is a continuation of application Ser. No. 07/368,717, filed on Jun. 21, 1989, which was abandoned upon the filing hereof.

BACKGROUND OF THE INVENTION

1. Field of the Invention

The present invention relates to an aroma generating device and more specifically, to a device in which aromatic ingredients discharged from a nozzle of the aroma generating device can be supplied with an air flow sent from an air conditioning apparatus.

2. Description of the Prior Art

As is well known, aroma generating devices are put in common residences, companies, factories, etc. in order to add fragrance to the air inside the buildings.

The above-mentioned aroma generating devices are composed of a compressed air supplying source, a container in which an aromatic is installed, and a nozzle. Moreover, the aroma generating devices with the above-mentioned composition are conventionally used by themselves. In practice, they supply the air inside a room with aromatic ingredients by discharging the compressed air from the compressed air supplying source through the aromatic container and the nozzle using the air sending power themselves.

On the other hand, various air-conditioning facilities have been developed for the purpose of cooling and heating the atmosphere or cleaning the air inside the buildings. These facilities have come into wide use as the air-conditioning units installed inside the building utilizes a central controlling system using ducts.

For example, the above-mentioned air-conditioning facilities are used to cool down or warm up the space inside the building by sending and circulating the air. Favorable temperatures inside the building (according to the season or temperature change of the air inside) are used for the purpose of keeping a pleasant environment.

Those conventional aroma generating devices as well as the above-mentioned air-conditioning equipment are excellent and include a long list of achievements when they are in general everyday use.

When the above-mentioned aroma generating devices are in use, they are inevitably required to distribute their fragrance widely and equally into the whole space inside the building.

In order to do so, a method to devise a nozzle was needed. The nozzle was widened or reformed into a shape like a harmonica but those reformations caused inconvenience because they tended to make the devices themselves bigger and large scaled. Moreover, they tended to make the cost of the devices higher so the improvement of those conditions has been expected.

SUMMARY OF THE INVENTION

The present invention was made in order to cope with the above-mentioned problems which the conventional technology could not solve. The purpose is to supply an aroma generating device using air-conditioning equipment which distribute its aromatic ingredients widely into the space inside the building by discharging them into the air sent from the air-conditioning equipment, This device does not need a nozzle to distribute its aromatic ingredients widely into the space inside the building, and it can therefore dispense with large size and at the same time reduce costs.

The present invention has the following technological methods to solve the above-mentioned problems:

When the explanation is given using the numbers and symbols on the appended figures which show the example of operations, an aroma generating device (A) in the present invention has characteristics as follows: it includes an aroma container (4) in which an aromatic (5) is installed and a nozzle (8) which is connected to the container, the aromatic ingredients from the aromatic (5) are discharged through the nozzle (8) into the space (P), and the abovementioned device (A), which makes use of the air-conditioning equipment, supplies the air sent from the ventilation system (12) of the air-conditioning equipment of the building with aromatic ingredients discharged from the nozzle (8) and the mixed air is sent into the space (P) inside the building.

With the above-mentioned composition taken, aromatic ingredients discharged from the nozzle (8) of the device (A) are circulated in the space (P) inside the building with the air sent from the ventilation system (12) of the air-conditioning equipment. Therefore, an effective addition of the aroma to the space P is executed widely and equally.

BRIEF DESCRIPTION OF THE DRAWINGS

The appended drawings show examples of the operation of the present invention

DESCRIPTION OF THE PREFERRED EMBODIMENTS

Next, a detailed explanation is given according to the appended drawings of the example operated on the present invention.

Figure 1:
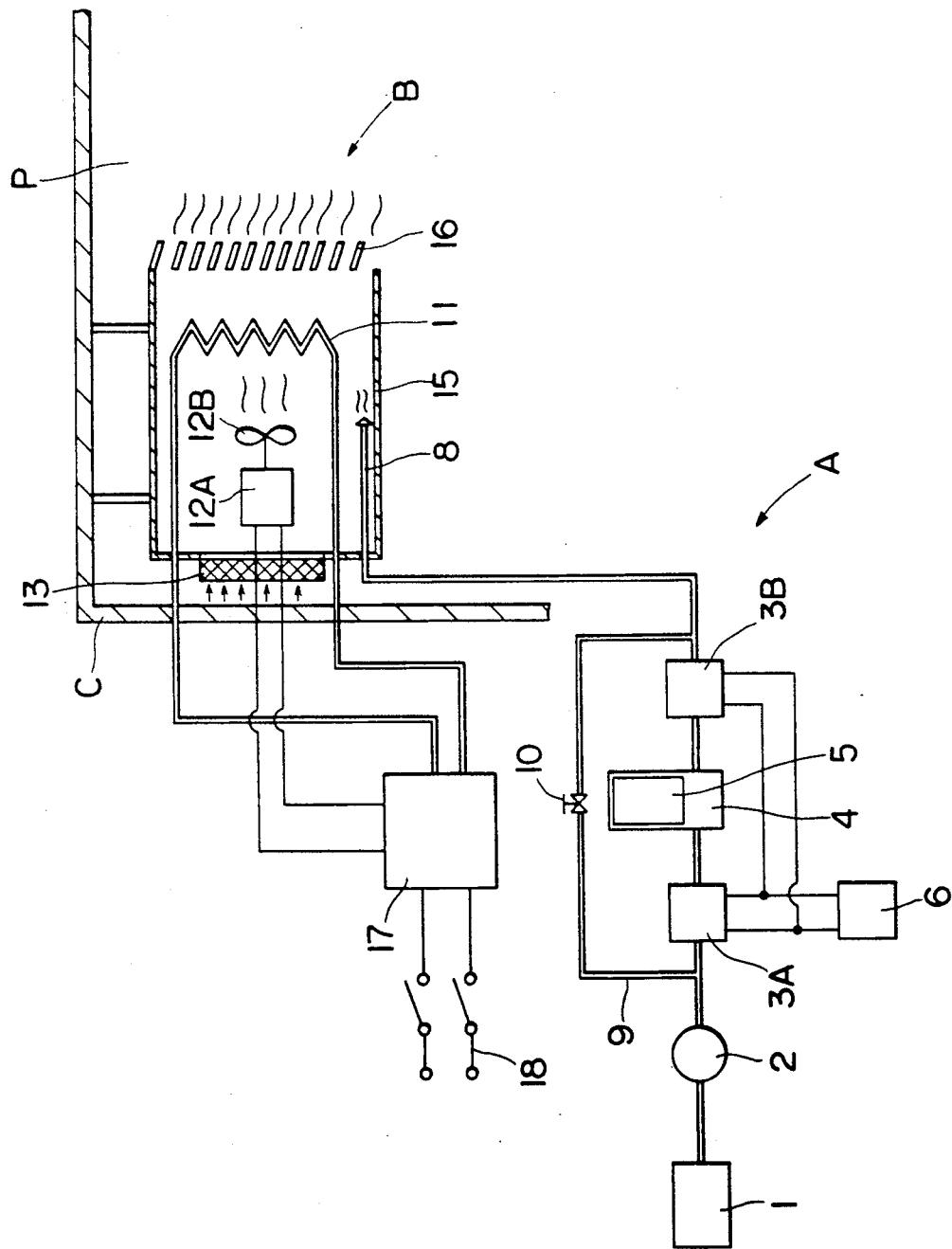
FIG. 1 and FIG. 2 show the first example and the second example of the operation using an air-conditioner, respectively.

The structural drawing was shown on FIG. 1 where an air-conditioner room unit is used as an air-conditioning equipment on the present invention.

The shape and the operation circuit of the air-conditioner as well as the aroma generating device itself are well known, so those are shown in a simplified way. As seen from the drawing, the present invention consists of an air-conditioner (B) which has an indoor unit (11) connected to an outdoor unit (17) and the aroma generating device (A). The device (A) is composed of a compressed air supplying source (1), an aroma container (4) in which an aromatic (5) is installed, and a nozzle (8) that, when in operation, can be controlled by a timer (6).

Moreover, a reducing valve (2) which reduces pressure of the compressed air sent from the compressed air supplying source (1), as well as electromagnetic valves (3a and 3b) which are put upstream of and downstream of the aroma generating container (4), control the opening and closing by a timer (6) (which has been installed).

Furthermore, a by-passing circuit (9) with an aroma amount adjusting valve (10) is installed from upstream stream of the electromagnetic valve (3A) to downstream of the electromagnetic valve (3B) so that it can adjust the aroma amount.

Though the above-mentioned aroma generating device (A) is only a method to discharge its aromatic ingredients of the aromatic (5), installing it in the indoor unit (11) (as is shown in the drawing) makes use of the air circulating power of the ventilation system (12) of the above-mentioned indoor unit (11). Practically, the device (A) is arranged so that it can supply the space (P) inside the building with the aromatic ingredients discharged from the nozzle (8) mixed with the air sent from a fan (12B) through the louver boards (16) of the indoor unit.

According to the structural drawing, (FIG. 1), the practical operation of the aroma generating device making use of the indoor unit of the air-conditioner is shown as follows.

At first, the compressed air sent from the compressed air supplying source (1) is reduced in pressure by the reducing valve (2) mixed with the aromatic ingredients of the aromatic (5) when passing through the aroma container (4), and discharged from the nozzle (8).

By reducing the pressure of the compressed air by the above-mentioned reducing valve (2), the noise generated when the air is discharged can be lowered. Moreover, the operation of the aroma generating device (A) is controllable during the air-conditioner's driving by switching it on and off every determined period of time.

By using the timer (6), when it is off, the upper stream electromagnetic valve (3A) as well as the lower one (3B) is closed and stops the electric current. On the other hand, when it is on, both of the valves (3A, 3B) are opened, connecting the electric current and letting the compressed air from the compressed air supplying source (1) flow into the aroma container (4) and discharge the aromatic ingredients. Furthermore, the strength of the fragrance is adjustable by adjusting the opening and closing level of the aroma amount adjusting valve (10) which is placed in the by-passing circuit (9). In this case, since the aroma generating device (A) is installed inside the internal unit (11) of the air-conditioner as a part of the unit, the aromatic ingredients are discharged from the nozzle (8) into the indoor unit (11). Moreover, sent by the ventilation system (12) of the indoor unit (11), the fragrance can be added effectively to the space (P) inside the building so it is not necessary to make the device bigger, or more specifically, to devise the nozzle (8) into a bigger one or into one with a harmonica shape in order to add the fragrance to the whole space (P) inside the building. The above method, therefore, enables its aroma generating device (A) to attain the purpose efficiently, only by discharging its aromatic ingredients from the nozzle (8). This also helps to lower the pressure of the compressed air and to eliminate the necessity of having a large size, therefore resulting in a reduction of costs.

Figure 2:
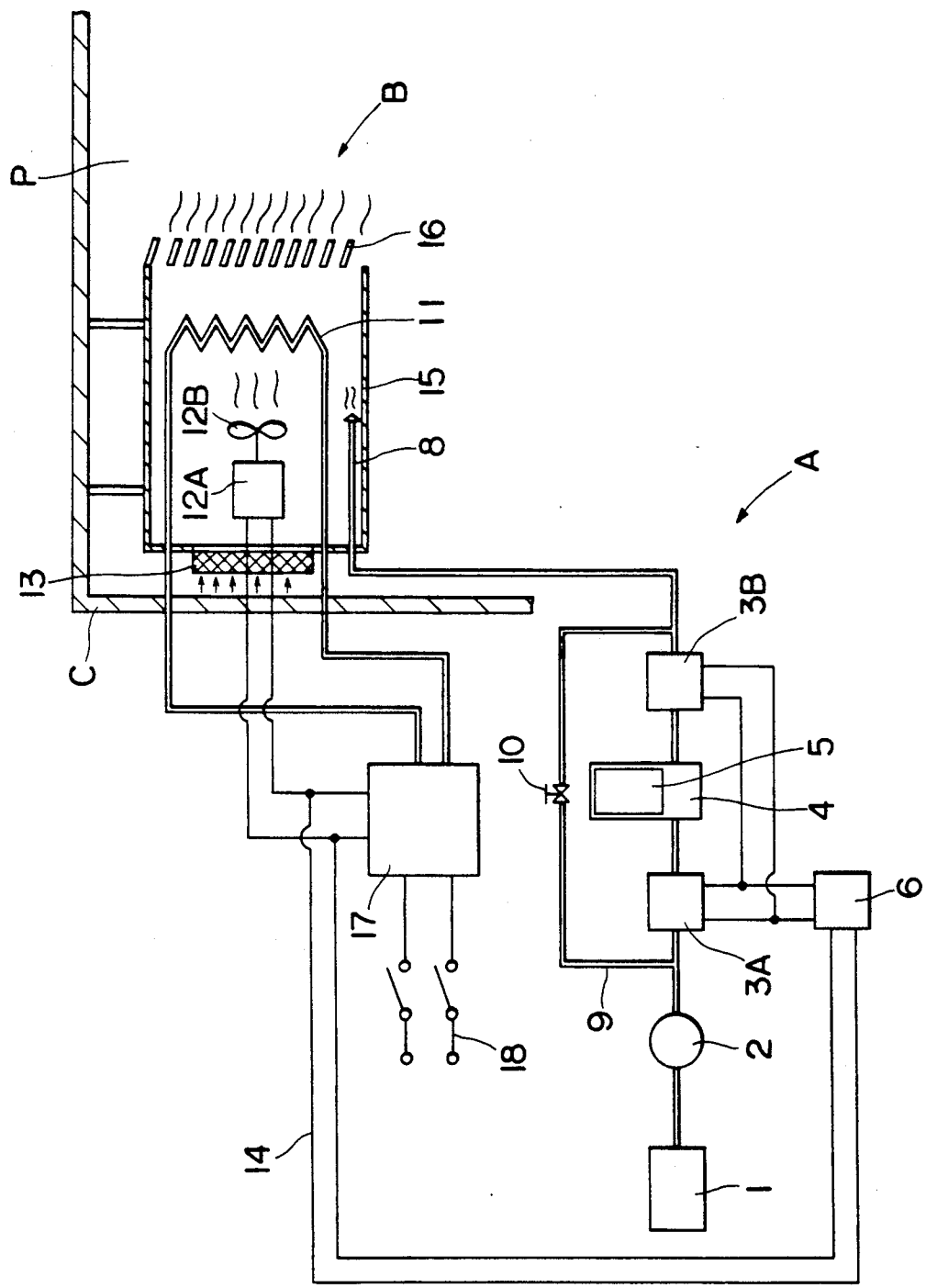

FIG. 2 is a structural drawing of the indoor unit of the air-conditioner showing an arrangement in which the ventilation system of the indoor air-conditioning device and the compressed air supplying source of the aroma generating device are electrically connected so that they can be operated at the same time.

A secondary circuit of the outdoor unit of the air-conditioner (B), and the aroma generating device (A), are electrically connected with wiring (14). The moment a power switch (18) of the air-conditioner (13) is turned on, electric current is led to the aroma generating device (4), making it under operation at the same time. This method makes it possible to finish the operation of switching on at one time, and makes the operation of the device more effective without leaving the switch on or off.

Moreover, in this example as well as the first example, the timer (6) set an operating time of the aroma generating device (A) so as to control the device and the by-passing circuit (9) with the aroma amount adjusting valve (10) can be used to adjust the amount of the fragrance.

The air-conditioner (B) itself is also automatically controlled by the outdoor unit (17) according to temperature inside the room. The fan (12B) of the indoor unit (11) automatically repeats its ventilating operation (on and off) making the device more effective. As to the compressed air supplying source (1), a compressor, a bomb, a blower, fan, etc. may be used, but the present invention doesn't specify the method.

Figure 3:
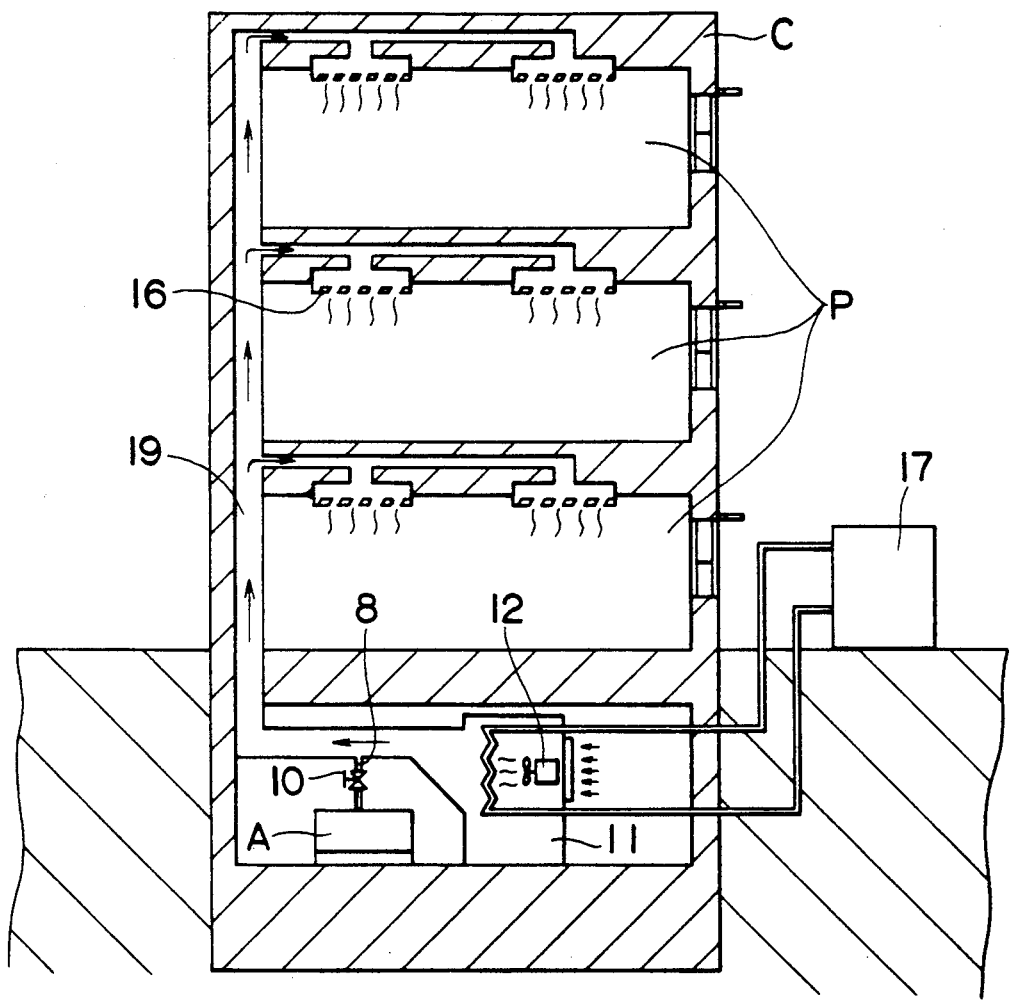
FIG. 3 shows an example of the operation when air-conditioning equipment with a central controlling system is used.

FIG. 3 shows a structural drawing of the device in which a central controlling method is taken as an air-conditioning apparatus.

An air-conditioning apparatus using a central controlling method is a system in which an indoor unit (11) and an outdoor unit (17) are used to control the air condition of the whole space (P) inside the building, by sending the air from a louvre (16) opened into the space (P) inside the building through a duct (19). The drawing is supposed to show the air-conditioning apparatus installed in a building with three stories above the ground and with a basement. Moreover, an aroma generating device (A) which has the same structure as that of the first example, consists of a compressed air supplying source (1), a reducing valve (2), an electromagnetic valve (3), an aroma container (7), a nozzle (8), a by-passing circuit (9), and an aroma amount adjusting valve, and it is place at the position where it can add fragrance to the air sent from a ventilation method (12) of an indoor unit (11).

According to the structural drawing (FIG. 3), the practical operation of the aroma generating device using a central controlling method as an air-conditioning apparatus is shown as follows:

The air modified its temperature by the ventilation method (12) of the indoor unit (11) is sent into the space (P) inside the building through the duct (19). By installing the nozzle (8) of the aroma generating device (A) inbetween the upstream side and the downstream side of this duct, the aromatic ingredients discharged from the nozzle (8) are led into the space (P) inside the building through the louvre (16).

Moreover, the air sending power of the ventilation system (12) of the indoor unit, which sends the air to the whole space inside the building, is comparatively big, so the aromatic ingredients are sucked out by reverse pressure. This makes it possible to dispense with the compressed air supplying source (1) of the aroma generating device (A), which checks the necessity of a large size and reduces the costs.

The aroma amount is also controllable by installing a valve (10) between the nozzle (8) and the aroma container (4), resulting in a possibility of omitting the by-passing circuit (9).

As the aromatic, various things can be suggested and some of them are as follows:

Natural perfumes; animal originas like Musk, ambergris, and plant life origins which are drained out by the vapor distilling from roots, trunks, branched, leaves, buds, flowers, fruits, or seeds, and artificial perfumes which are obtained by the synthetic reaction like oxidation or condensation from extracted perfumes or pure compositive materials like tar system or petro-chemical products.

As the plant life origina perfumes, the following examples are shown: citronella oil, camphor oil, lemon oil, lemon grass oil, orange oil, peppermint oil, eucalyptus oil, lavender oil, bergamot oil, spearmint oil, lime oil, peti-grain oil, ylang-ylang oil.

As the artificial perfumes, benzene system synthetic perfumes, artificial musk, system synthetic perfumes are listed as examples.

Advantages to be obtained:

The present invention, which is composed of the abovementioned arrangements, has the advantages described as follows:

Because an air-conditioning apparatus is made use of in this method, the aromatic ingredients are distributed widely within the space inside the building and it is not necessary to remodel the shape of the nozzle. Therefor, it has various practical advantages in eliminating the necessity of having a large size, reducing its the cost, etc.

In the one case wherein an inside unit of an air-conditioner is used as an air-conditioning apparatus (since the unit is widely used in a common room, etc.) the aroma generating device which is appropriate for general use and also has the above-mentioned advantages, can be supplied.

In the other case where in a central controlling method of an air-conditioning apparatus (widely installed in buildings, factories, etc.) is used the device is uniquely suitable for use in those places.

The ventilation system of the air-conditioner's inside unit described above and the compressed air supplying source of the aroma generating device are electrically connected by wiring so that they can be operated at the same time one operation is able to switch on or off both the aroma generating device and the air-conditioner, resulting in an effective use of the aroma generating device.

What we claim is:

1. An aroma generating apparatus to be used in conjunction with an air-conditioner unit including a box-like casing, an internal fan located inside a space defined by said box-like casing, and louvered vents that discharge conditioned air to an area to be conditioned, said aroma generating apparatus comprising:

a source of compressed air;
   means for adjusting pressure of the compressed air;
   an aroma container containing an aromatic;
   a compressed air passage extending between said source of compressed air and an air conditioning chamber defined by said box-like casing and disposed proximate said louvered vent, said compressed air passage passing through said aroma container so that gaseous aromatic is carried by the compressed air into said air conditioning chamber;
   a bypass air passage connected to said compressed air passage at positions upstream and downstream of said aroma container, said bypass air passage allowing at least part of the compressed air to bypass the aroma container; and
   valve means disposed in said compressed air passage means for selectively permitting and blocking flow of the compressed air through said aroma container for adjusting a proportion of said gaseous aromatic in the conditioning air within said conditioning chamber.

2. Apparatus as in claim 1, further comprising first and second electromagnetic valves, said first electromagnetic valve being attached to said compressed air passage between said source of compressed air and said container and said second electromagnetic valve being located between said container and said casing, said first and second electromagnetic valves being timer-controlled.

3. Apparatus as in claim 1, wherein said apparatus further comprises a valve that can adjust degree of aroma exiting from the compressed air passage into the casing.

4. Apparatus as in claim 1, wherein the air-conditioner and aroma generating apparatus are seperate units.

5. An aroma generating apparatus for use with an air conditioner unit including a box-like casing, an internal fan located inside of a space defined by said box-like casing, and louvered vents that discharge conditioned air to an area to be conditioned, said aroma generating apparatus comprising:

a source of compressed air;
   means for adjusting pressure of the compressed air;
   an aroma container containing an aromatic;
   a compressed air passage extending between said compressed air source and an air conditioning chamber defined by said box-like casing, said chamber being positioned proximate said louvered vents, said compressed air passage passing through said aroma container so as to carry gaseous aromatic with said compressed air into said air conditioning chamber;
   a bypass air passage connected to said compressed air passage at positions upstream and downstream of said aroma container, said bypass air passage permitting at least part of the compressed air to bypass said aroma container;
   valve means disposed in said compressed air passage for selectively permitting and blocking flow of said compressed air through said aroma container so as to control a proportion of said gaseous aromatic in the compressed air entering said conditioning chamber; and
   a nozzle disposed, on one end of said compressed air passage remote from said compressed air source and disposed within said air conditioning chamber inside the casing, said nozzle serving as an exit for compressed air containing the aromatic, said nozzle disposed so that air exiting therefrom is disposed proximate the internal fan.

6. An aroma generating apparatus for use with an air conditioner unit including a box-like casing, an internal fan located inside of a space defined by said box-like casing, and louvered vents that discharge conditioned air to an area to be conditioned, said aroma generating apparatus comprising:

a source of compressed air;
   means for adjusting pressure of the compressed air;
   an aroma container containing an aromatic;
   a compressed air passage extending between said compressed air source and an air conditioning chamber defined by said box-like casing and positioned proximate said louvered vents, said compressed air passage passing through said aroma container so as t carry gaseous aromatic with said compressed air into said air conditioning chamber;
   a bypass air passage connected to said compressed air passage at positions upstream and downstream of said aroma container, said bypass air passage permitting at least part of the compressed air to bypass said aroma container;

valve means disposed in said compressed air passage for selectively permitting and blocking flow of said compressed air through said aroma container so as to adjust a proportion of said gaseous aromatic in the compressed air entering said chamber;

timer means for controlling timing of operation of said valve means between a first position permitting said compressed air to flow through said aroma container and a second position preventing said compressed air from flowing through said aroma container; and a nozzle provided on one end of said compressed air passage remote from said compressed air source and disposed within said chamber inside the casing of the air-conditioner, said nozzle serving as an exit for compressed air containing the aromatic, said nozzle being positioned so that air exiting therefrom is disposed proximate the internal fan.

7. An aroma generating apparatus for use with an air conditioner unit including a box-like casing, an internal fan located inside of a space defined by said box-like casing, and louvered vents that discharge conditioned air to an area to be conditioned, said aroma generating apparatus comprising:

a source of compressed air;

means for adjusting pressure of the compressed air;

an aroma container containing an aromatic;

a compressed air passage extending between said compressed air source and an air conditioning chamber defined by said box-like casing and positioned in the vicinity of said louvered vents, said compressed air passage passing through said aroma container so as to carry gaseous aromatic with said compressed air into said air conditioning chamber;

temperature adjusting means including a first part disposed in the external atmosphere and a second part disposed in said air conditioning chamber so as to adjust the temperature of the conditioning air within said air conditioning chamber relative to the external atmosphere;

a bypass air passage connected to said compressed air passage at positions upstream and downstream of said aroma container, said bypass air passage means permitting at least part of the compressed air to bypass said aroma container;

valve means disposed in said compressed air passage for selectively permitting and blocking flow of said compressed air through said aroma container so as to adjust a proportion of said gaseous aromatic in the compressed air entering said conditioning chamber;

timer means for controlling timing of operation of said valve means between a first position permitting said compressed air to flow through said aroma container and a second position blocking said compressed air from flowing through said aroma container, said timer means cooperating with said temperature adjusting means so as to synchronize operation of said valve means therewith; and a nozzle provided on one end of said compressed air passage means remote from said compressed air source and disposed within said air conditioning chamber inside the casing of the air-conditioner, said nozzle serving as an exit for compressed air containing the aromatic, said nozzle being positioned so that air existing therefrom is disposed near the internal fan.

8. An aroma generating apparatus in combination with an air conditioner, comprising:

an air conditioner including a casing defining an internal chamber, an internal fan disposed in said chamber and louvered vents that discharge conditioned air to an area;

a source of compressed air;

means for adjusting pressure of the compressed air;

means for containing an aromatic;

a compressed air passage extending between said source and said chamber, said compressed air passage opening proximate said louvered vents, said compressed air passage passing through said containing means so that gaseous aromatic may be carried into said chamber by the compressed air;

a bypass passage connected to said compressed air passage at positions upstream and downstream of said containing means, said bypass passage allowing at least part of the compressed air from the source to not pass through said containing means; and valve means disposed in said bypass passage for selectively allowing compressed air to flow through said containing means, thus allowing adjustment of aromatic flow into said chamber.

* * * * *